United States Patent
Ng

[19]

[11] Patent Number: 5,807,283
[45] Date of Patent: Sep. 15, 1998

[54] ACTIVITY MONITOR

[76] Inventor: Kim Kwee Ng, P.O. Box 379, Selden Post Office, Selden, N.Y. 11784-0379

[21] Appl. No.: 789,525

[22] Filed: Jan. 27, 1997

[51] Int. Cl.$^6$ ...................................................... A61B 5/00
[52] U.S. Cl. ............................................................ 600/595
[58] Field of Search ..................................... 600/587, 595, 600/592

[56] References Cited

U.S. PATENT DOCUMENTS

| | | | |
|---|---|---|---|
| 4,416,293 | 11/1983 | Anderson et al. | 600/595 |
| 4,651,446 | 3/1987 | Yukawa et al. | 36/132 |
| 4,737,774 | 4/1988 | Chapman et al. | 340/573 |
| 4,813,436 | 3/1989 | Au | 600/595 |
| 5,484,362 | 1/1996 | Skowronski et al. | 482/54 |
| 5,485,402 | 1/1996 | Smith et al. | 364/566 |

*Primary Examiner*—Max Hindenburg

[57] ABSTRACT

An electronic device for monitoring the activity of a wearer, his walking speed as well as the distance traversed in a selected time interval. The invention comprises a magnet strapped to a leg of a person or a shoe of a pair, a Hall effect sensor with its associated electronic processing and display accessories mounted on the other leg of the person or the other shoe of the same pair. When the sensor moves past the magnet, the analog Hall output voltage produced by the Hall effect sensor changes. A series of these analog Hall output voltages produced during relative motion of the magnet and the sensor are converted to binary data. A stored program device means is used to analyze the data to yield information about the distance traversed and the speed of relative motion between the magnet and the sensor. Remote means receives analog radiowave signals encoding the digital values permitting distant monitoring of the gait activity of the wearer of the gait activity monitor of this invention. A simplified electronic circuit activates a plurality of display elements whenever there is a relative movement between the magnet and the sensor. By mounting a plurality of magnetic strips on an athletic field track, the activity of a runner wearing a magnetic-sensitive sensor with its electronic computing circuit can be monitored.

17 Claims, 2 Drawing Sheets

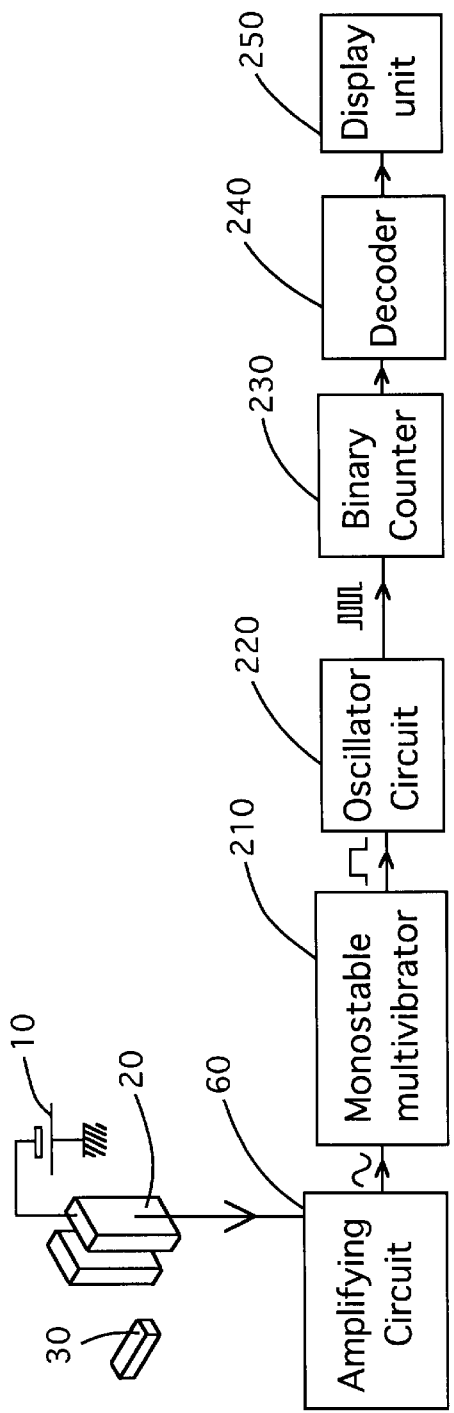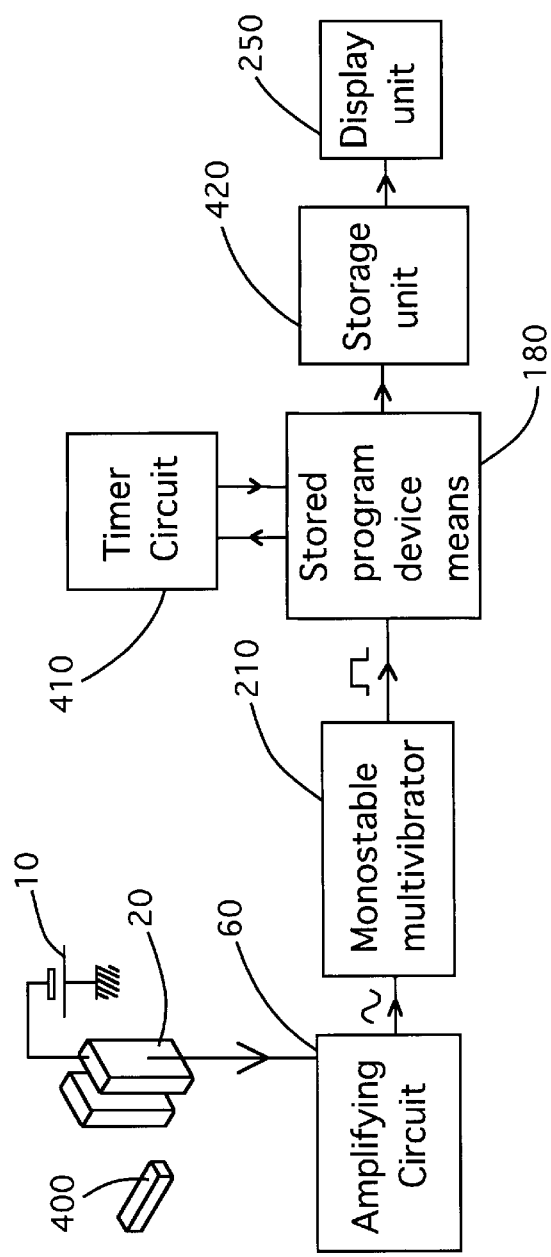

ACTIVITY MONITOR

FIELD OF THE INVENTION

This invention is related to the measurement of an activity of a person using an electronic means employing a magnetic-sensitive control circuit or a Hall effect sensor.

DESCRIPTION OF THE PRIOR ART

U.S. Pat. No. 5,485,402, "Gait activity monitor" describes the use of an electronic accelerometer for producing signals for transmission through an optical transmitter in conjunction with a computer for monitoring gait activity of a wearer. A monitor of that invention determines and records the number of steps taken by a wearer during selected time intervals. U.S. Pat. No. 4,651,446, "Electronic pedometer", describes the use of a step sensor and an electric counter associated with a footwear. The step sensor senses a flexing motion of the footwear each time the footwear contacts the ground. An electronic counter including a computing circuit receives output from the sensor and computes the number of steps and the distance traversed. The resulting measurement is shown on a visual display device.

SUMMARY OF THE INVENTION

In a first embodiment of my invention, an electronic device comprises a magnet strapped to a leg of a person or a shoe of a pair and a Hall effect sensor with an associated electronic processing and display unit mounted on the other leg of the person or the other shoe of the same pair. As the magnet moves past the sensor, the analog Hall voltage output produced by the Hall effect sensor changes with the motion because the strength of the magnetic field differs as a function of the separation between the magnet and the sensor. The analog voltage signals from the Hall effect sensor are converted to digital data and a stored program device means is used to analyse the data to yield digital values for the distance traversed and the speed of relative motion between the magnet and the sensor. Remote means receives analog radio signals encoding the digital values permitting distant monitoring of the gait activity of the wearer of the gait activity monitor of this invention.

In a second embodiment of my invention, a simplified electronic circuit activates a plurality of display elements whenever there is a relative movement between the magnet and the sensor. In another embodiment of my invention, when a magnetic-sensitive sensor carried by a runner moves past a magnetized strip mounted on an athletic field track, a timer circuit is triggered. When the runner passes the magnetized strip again, the timer circuit is similarly triggered. The time elapsed between the triggerings and the average running speed can be calculated and displayed.

It is an object of this invention to provide a measurement of the distance traversed by a carrier carrying an electronic device of this invention comprising a Hall effect sensor, a magnet and appropriate electronic processing and display accessories. Utilizing the well known Hall effect, (i.e. the output voltage generated by the sensor varies with the strength of the magnetic field detected by the Hall sensor), it is possible to compute the distance separating the magnet and the sensor. The result is displayed by an information display unit. Speed of movement as well as the activity of the wearer can be monitored remotely by this invention.

BRIEF DESCRIPTION OF THE DRAWING

FIG. 3 is a simplified block diagram of a preferred embodiment of the invention using a monostable multivibrator to control a plurality of display elements.

FIG. 4 is a simplified block diagram of a preferred embodiment of the invention using a timer circuit for counting.

DESCRIPTION OF THE PREFERRED EMBODIMENT

Figure 1:
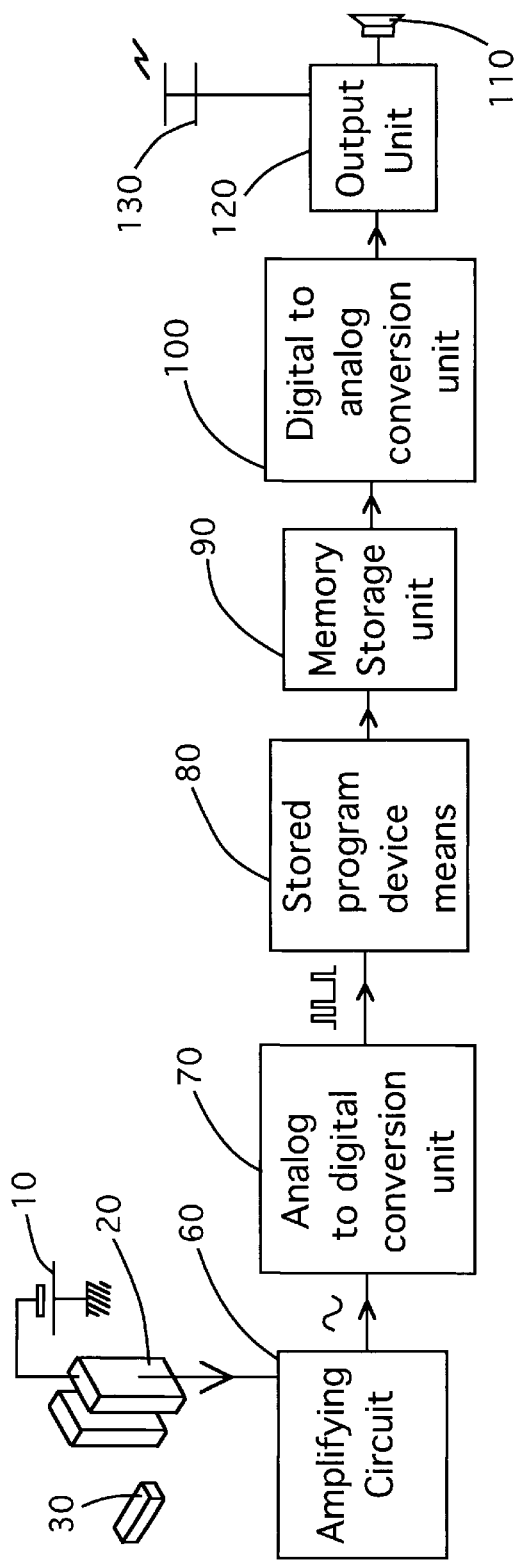
FIG. 1 is a simplified block diagram of a preferred embodiment of the invention using Hall-effect sensors with associated electronic circuits.

In a first preferred embodiment of my invention for use with a power source means, 10, shown in FIG. 1, an array of Hall-effect sensors 20 strapped to a leg of a person or a shoe of a pair, generates an analog Hall effect voltage signal in the presence of a magnetic field produced by a magnetic field-generating source, e.g. a magnet, 30, mounted on another leg of the person or the other shoe of the same pair and positioned with its magnetic axis parallel to an axis orthogonal to the planar surfaces of sensor array 20 as shown in FIG. 1. When the Hall effect sensor array 20 moves past the magnet 30, the Hall voltage changes in response to the change in the strength of the magnetic field the Hall effect sensor array 20 senses. The change in the voltages is amplified by an Amplifying Circuit 60. The amplified output voltage produced by the Amplifying Circuit 60 is sent to an Analog to Digital Conversion Unit 70 for conversion, so that the amplitude of this output voltage is encoded in a binary data form. A series of these binary data accumulated over time during which the sensor array 20 moves past the magnet 30 is processed by a stored program device means 80, comprising a processor and its associated computing unit, which in turn produces useful information about the distance separating the magnet 30 and the sensor array 20, as well as its relative moving speed. This is obvious because the strength of the magnetic field at a given point depends on its distance from the magnet 30, so the output voltage produced by a Hall effect sensor array 20 varies according to its distance from the magnet 30. The rate of change in the amplitude of the output voltage determines the relative speed of the motion of the Hall effect sensor array 20 with respect to the magnet 30.

When the Hall effect sensor array 20 and the magnet 30 move past each other several times, the voltage produced by the sensor array 20 resembles a crude sinusoidal waveform. The difference between the crest and the lowest point of this waveform in a selected time interval tells us about the distance it has traversed during that period of time interval, the tangency of the curve at different point of this waveform indicates the speed of the movement of the sensor array 20 with respect to the magnet 30. The output from the stored program device means 80 is stored in a Memory Storage Unit 90. The result stored in the Memory Storage Unit 90 is either displayed by various types of display elements, such as LEDs, light-emitting diodes, or processed by a Digital to analog conversion unit 100 to yield an announcement through a speaker 110 in an Output Unit 120, using, for example, a sound synthesizer or a programmable music producing unit, or a radiowave transmitting device with a radiowave-emitting antenna 130, as is well known in the art, encoding the gait activity data in a radiowave carrier. The digital results are shown in the traditional numeric data form as well as in the form of blinking LEDs mounted on the shoe at a frequency proportional to the relative speed of the movement of the sensor array 20 with respect to the magnet 30.

Figure 2:
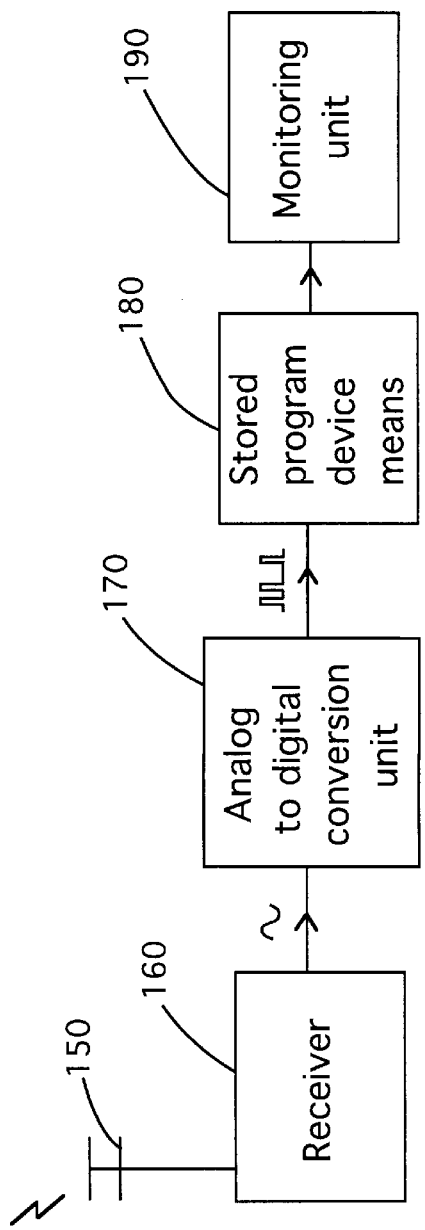
FIG. 2 is a simplified block diagram of a partial embodiment of the invention using electronic circuits to process radiowave signals emitted from the output device of FIG. 1.

Referring now to FIG. 2 which shows a partial embodiment of my invention for use with the electronic device of FIG. 1, wherein the Output Unit 120 of FIG. 1 comprises a radiowave-emitting device, which emits radiowave signals providing the electronic information about the gait activity of a wearer of the device comprising a magnet 30 and a Hall effect sensor array 20 of FIG. 1. Radiowave signals received by an antenna 150 of a receiver 160 are amplified and processed by a signal-decoding Analog to digital conversion unit 170. A stored program device means 180 is used to process the data produced from the Analog to digital conversion unit 170. The output is sent to a Monitoring Unit 190. The Monitoring Unit 190 comprises information display elements as is well known in the art, as well as a sound-emitting device alerting a monitor of abnormal incidences. For example, when the wearer of the electronic device of FIG. 1 is about to go out of a pre-determined monitoring range as the radiowave signals emitted from the Output Unit 120 of FIG. 1 becomes weaker and drops below a preset threshold value, or the wearer is inactive for a prolonged period of time, an alarm will sound. The stored program device means 80 of FIG. 1 is programmed to encode the radiowave signals produced by the Output Unit 120 with an identifier uniquely identifiable to the wearer. The stored program device means 180 is programmed to monitor activities of one or more carriers carrying electronic devices of FIG. 1.

Referring now to FIG. 3 which shows a second preferred embodiment of my invention adapted for use with a monostable multivibrator 210, wherein like symbols of FIG. 1 and FIG. 3 refer to like elements. The Hall voltage changes when a Hall effect sensor array 20 moves past a magnet 30. The change in the Hall voltages is amplified by an Amplifying Circuit 60. The amplified output voltage from the Amplifying Circuit 60 triggers a process controller or a control circuit, e.g. a monostable multivibrator, 210, which produces a pulse with a proper time interval during which an Oscillator Circuit 220 generates a series of square-wave pulses. Each of these square-wave pulses accumulates a count in a Binary Counter 230. The result in the counter 230 is decoded by a Decoder Circuit 240 which allows a one of an array of display elements in a Display Unit 250 to light up. If the count in the Binary Counter 230 is increasing monotonically, each of the display elements, e.g. an LED, is lit according to its position in the Display Unit 250. So a simple rotating lighting pattern occurs if the LEDs are arranged in sequence in a loop according to the binary data in the Binary Counter 230. A different lighting pattern occurs regularly if the LEDs are not arranged in sequence in the loop.

Referring now to FIG. 4 of the drawings, a third preferred embodiment of my invention showing an electronic circuit for monitoring the activity of a runner, wherein like symbols of FIG. 4, FIG. 1 and FIG. 3 refer to like elements. When a person carrying a magnetic-sensitive sensor, e.g. a Hall effect sensor array 20, moves past a magnetized strip 400 mounted or embedded in an athletic field track or a runway, the Hall voltage produced by the sensor array 20 changes. The change in the Hall voltages is amplified by an Amplifying Circuit 60. The amplified output from the Amplifying Circuit 60 triggers a monostable multivibrator 210 which produces a pulse notifying a stored program device means 180. The stored program device means 180 activates a Timer Circuit 410 which starts a process of counting. When the runner wearing the sensor array 20 passes the magnetized strip 400 again, the stored program device means 180 is similarly triggered again. The stored program device means 180 retrieves the digital values of the time elapsed between triggerings from the Timer Circuit 410. The average running speed, based on a pre-determined running distance, is computed and stored in a Storage Unit 420. The Storage Unit 420 comprises an array of non-volatile memory, as well as re-writable diskettes or the like. The results, including the number of excessive triggerings indicating the number of turns the runner has circled the athletic field, are displayed by a plurality of display elements in a Display Unit 250. It is clear that a plurality of magnetized strips 400 can be mounted on a runway, the times elapsed between successive triggerings can be computed and displayed. It is also obvious that a magnet could be strapped to a leg of a person or a shoe, a plurality of sensor arrays 20 with electronic processing circuits can be mounted at different locations along a field track. A stored program device means 180 is preprogrammed to process data produced from the sensor arrays 20 with associated electronic circuits. The results are displayed by Display unit 250.

Having described the invention and its preferred modes of operation in sufficient detail for those of normal skill in the art to practice the same, it will be obvious to such practitioners to make certain changes and variation in the specific elements of the disclosed embodiment without departing from the scope of the invention. For example, an electronic circuit generating a magnetic field can be used for sensing by the Hall effect sensors. Upon sensing the change in the magnetic field as the sensor moves past the magnet, the sensor with its control circuit activates a plurality of switching elements, mechanical or otherwise, to control the display elements. It is also obvious that a magnetic-sensitive control switch, e.g. a magnetic relay switch, can be used to turn on or off the power supply to the display elements when a magnet moves close to or away from the magnetic relay switch. For these reasons, the scope of the invention should not be limited by that which has been illustrated herein but should be limited only by the scope of the appended claims:

I claim:

1. An electronic device for displaying information about the running speed and distance trasversed by a person, comprising:
   a) a first means mounted on a first leg for producing a magnetic field;
   b) a second means mounted on a second leg for generating an analog voltage in response to said magnetic field detected by an array of Hall-effect sensors;
   c) means coupled with said second means for converting said analog voltage to binary code; and,
   d) means for processing said code to display said information.

2. The device of claim 1, wherein said device includes means defining a radiowave-emitting device.

3. The device of claim 1, wherein said device includes means defining a sound producing system.

4. The device of claim 2, wherein said device includes means defining a radiowave receiver and monitoring unit.

5. An electronic device for displaying information about the activity of a runner in an open field, comprising:
   a) a first means mounted on a first leg for producing a magnetic field;
   b) a second means mounted on a second leg to detect changes in said magnetic field;
   c) control circuit means defining a process controller activated by said second means to start pulse generation, trigger control and data processing; and,
   d) means defining a plurality of display elements.

6. The device of claim 5, wherein said second means comprises a plurality of Hall-effect sensors.

7. The device of claim 5, wherein said second means comprises a plurality of magnetic-sensitive relay switching elements.

8. The device of claim 5, wherein said device includes means defining a plurality of pulse generators for producing a plurality of pulses and a digital counter and decoder for counting and decoding said pulses.

9. The device of claim 5, wherein said device includes a stored program device means for processing data from said process controller.

10. The device of claim 5, wherein said device includes a timer circuit for counting time after triggering by said control circuit means.

11. An electronic means for displaying information about the running speed and distance trasversed by a moving person, employing a first device and a second device, comprising:

a) said first device comprising a plurality of source means for producing a magnetic field;

b) said second device comprising a plurality of sensor means for detecting changes in said magnetic field;

c) means, associated with said moving person, whereby said first device activates said second device to detect a varying said magnetic field;

d) a stored program device means for processing data from said second device; and, e) means defining a plurality of display elements.

12. The invention of claim 11, wherein said first device is mounted on a leg and said second device is mounted at a desired location adjacent to a running track.

13. The invention of claim 11, wherein said first device is mounted at a desired location adjacent to a running track and said second device is mounted on a leg.

14. The invention of claim 11, wherein said sensor means comprises a plurality of Hall-effect sensors for generating analog voltages.

15. The invention of claim 11, wherein said sensor means comprises a plurality of magnetic-sensitive relay switching elements.

16. The invention of claim 14, wherein said electronic means includes means for converting said analog voltages to binary code.

17. The invention of claim 11, wherein said electronic means includes a timer circuit for counting time after triggering by said second device.

* * * * *